United States Patent [19]

Michaeli

[11] Patent Number: 4,745,098
[45] Date of Patent: May 17, 1988

[54] COMPOSITIONS AND METHOD FOR IMPROVING WOUND HEALING

[75] Inventor: Dov Michaeli, San Francisco, Calif.

[73] Assignee: The Regents of the University of California, Berkeley, Calif.

[21] Appl. No.: 583,159

[22] Filed: Feb. 24, 1984

[51] Int. Cl.$^4$ .................. A61K 37/00; A61K 31/725; A61K 31/715
[52] U.S. Cl. ........................................ 514/2; 514/56; 514/54; 514/822
[58] Field of Search ................. 424/177, 183; 536/21; 514/54, 56, 2

[56] References Cited

U.S. PATENT DOCUMENTS

| | | | |
|---|---|---|---|
| 4,060,081 | 11/1977 | Yannas et al. | 128/156 |
| 4,350,629 | 9/1982 | Yannas et al. | 260/123.7 |
| 4,418,691 | 12/1983 | Yannas et al. | 128/156 |
| 4,448,718 | 5/1984 | Yannas et al. | 260/123.7 |

FOREIGN PATENT DOCUMENTS

| | | |
|---|---|---|
| 6652 | 1/1969 | France . |
| 2362632 | 3/1978 | France . |
| 1205609 | 9/1970 | United Kingdom . |

OTHER PUBLICATIONS

Yannas et al., Stage 2 Artificial Skin: A Polymeric Template for Regeneration of New Skin, Chem Abstracts 99: 110713m (1982).
Danielsen, Mechanical Properties of Reconstituted Collagenfibrils, Influence of a Glycosaminoglycan: Dermatan Sulfate, Chem Abstracts 98:1845q (1982).
Yannas et al., Design Principles and Preliminary Clinical Performance of an Artificial Skin, Chem Abstracts 97: 115299z (1982).
Jungneira et al., Correlation of Specific Sulfated Glycosaminoglycans with Collagen Types I, II and III, Chem Abstracts 95:21810r (1981).
Gallagher et al., Synthesis of Glycosaminoglycans by Human Skin Fibroblasts Cultured on Collagen Gels, Chem Abstracts 93: 235868y (1980).
Dagalakis et al., Design of an Artificial Skin, Part III, Control of Pore Structure, Chem Abstracts 93: 225595t (1980).
Stryer: Biochemistry (2nd ed.), pp. 200-203 (1981).
Nature 297:307, 1982; S. Taylor et al., "Protamine is an Inhibitor of Angiogenesis".
Science 721:719, 1983; J. Folkman et al., "Angiogenesis Inhibition Caused by Heparin in the Presence of Cortisone".
Journ. of Biomed. Materials Research 14:511 1980—N. Dagalakis et al., "Design of an Artificial Skin".
Technology Review–May/Jun. 1981; pp. 79-81.
Ann. Surgery 194:413 1981; J. Burke et al.
Journ. of Biomed. Materials Research 14:107–1980, I. Yannas et al.
Journ. of Biomed. Materials Research 14:65—1980; I. Yannas et al.
Cancer Research 43:1790—1983—G. Alessandri et al.
J. Clinical Investigations 62:916 et seq. 1978 T. M. Chiang et al.

Primary Examiner—J. R. Brown
Assistant Examiner—John W. Rollins
Attorney, Agent, or Firm—Phillips, Moore, Lempio & Finley

[57] ABSTRACT

The healing of wounds is promoted by contacting the wound surfaces with a suspension of collagen and a glycosaminoglycan that is chemotactic for fibroblasts and/or endothelial cells. Typical glycosaminoglycans that exhibit the desired chemotaxis are heparin, heparan sulfate, and alginate. Two or more glycosaminoglycans can be present in the suspensions. Collagen is present in the suspension in the order of 7-10 mg/ml; while the glycosaminoglycan is present in much lower concentrations, e.g., 250-350 µg/ml. Application of the collagen/glycosaminoglycan suspension to open wounds greatly increases the rate of healing.

46 Claims, No Drawings

COMPOSITIONS AND METHOD FOR IMPROVING WOUND HEALING

BACKGROUND OF THE INVENTION

Human skin is a major organ of the body. It is a complex organization of specialized tissue cells, vascular blood supply networks, nerves, glands, lymphatic system, etc. all of which interact to form the interface between the internal organism and the surrounding environment. In this regard the skin forms a barrier between the body and the environment; with one of its principal functions being the protection of the body from invasion by potentially hazardous materials and organisms. The skin's integrity is therefore all important to the continued well-being of the individual, and any breach or rupture represents a threat that must be met by the body in order to protect its contained existence.

Breaches or ruptures in the skin's integrity can be caused by external physical forces such as blows, cuts, missiles etc., that penetrate and disrupt the skin barrier; or by degenerative internal processes occasioned by disease, congenital anomalies or changes in biochemical systems which result in abscesses, or ulceration that breach the skin barrier.

Under normal circumstances the body provides mechanisms for the repair and eventual healing of the rupture or breach to thereby restore the integrity of the skin barrier.

The repair process for even minor breaches or ruptures takes a period of time extending from hours and days to weeks; and in some instances, as in ulceration, the breach or rupture may persist for extended periods of time, i.e., months or even years. At all times, whether brief or extended, the potential for invasion by pathogenic organisms or foreign substances continues until new tissue has been generated to fully close the rupture or breach.

Because of the danger of infection, the customary management of wounds includes an initial thorough cleansing of the affected area to remove any contaminants such as dirt, clothing particles, or other debris which may introduce pathogenic materials. Any hopelessly damaged tissues may be debrided and antiseptic materials are applied to make the area as sterile as possible. If considered necessary, sutures may be used to reduce the area of the underlying tissues and thereby limit the amount of tissue exposed to subsequent contamination.

Ordinarily sterile dressings are applied to the affected area to maintain as clean and sterile an environment as possible. The dressings are periodically removed to permit the application of antiseptics and further cleansing of undesirable exudates if present. Further dressings are then applied until the tissue rebuilding mechanisms can begin the healing process.

The healing process is brought about by complex biological mechanisms generally involving several groups of special cells and proteins. Leucocytes, such as neutrophils and macrophages, crowd the wound site and digest foreign pathogens and debris. Such cells also send out chemical signals that marshal fibroblasts in the wound vicinity and ultimately generate connective structures, principally, collagen, which make up a major portion of the new tissues. Endothelial cells generate new blood capillaries that grow into the reconstructed tissue areas where their presence is necessary to supply nutrients to the newly growing tissue cells and remove catabolic products. As the new capillaries grow, the cells on the margin of the wound simultaneously multiply and grow inwardly. The fibrous tissue arising from this cell growth eventually fills the wound cavity with a network of interlacing threads of collagen which in due time, arrange themselves in firm bands and form the permanent new tissue.

The surface of the wound subsequently is covered by a process of enlargement, flattening, and multiplication of the surface, or epithelial cells at the wounds' edge. These epithelial cells spread as sheets into the wound, beneath the scab. Eventually the proliferating epithelial cell sheets emanating from the wound sides coalesce to cover and close the wound on the outer surface.

All of the above noted healing processes take considerable time. The rate of healing is influenced by the wound's freedom from infection, the general health of the individual, and presence of retained foreign bodies, or the like. For healthy individuals with no complications, the completion of healing nonetheless can take a considerable period of time, i.e., days to weeks. In some instances, the healing process can be impaired by constitutional deficiencies, or by disease processes, and healing may never effectively take place.

Until such time as at least superficial healing has occurred, or if healing is impaired, the individual remains at risk from continued or new infection. Therefore there is a time/rate related risk factor attendant to all wound situations. The quicker the wound can heal, the sooner the risk is removed. Thus any procedure that can influence the rate of wound healing, or even favorably influence the healing of intractible wounds, would be of great value.

BRIEF DESCRIPTION OF THE INVENTION

The present invention relates to compositions and procedures that improve the ability of wounds to heal and/or increase the rate at which wounds heal.

More specifically, the present invention presents compositions which, when applied to wounds, greatly enhance and promote the normal healing processes. Such compositions comprise suspensions of a mixture of the fibrous protein, collagen; and a polysaccharide, glycosaminoglycan.

In the process of the invention, the collagen/glycosaminoglycan suspension is applied to the wound and maintained in contact therewith for an extended period, i.e., during the entire healing process, or until at least closure of the wound by new tissue has taken place.

The application of the collagen/glycosaminoglycan suspension promotes the vascularization of the wound, attracts fibroblasts and endothelial cells by chemotaxis, and generally provides a favorable environment for the cells that participate in the healing process.

It is therefore an object of the invention to provide compositions that promote the tissue healing process.

It is another object of the invention to provide a method for promoting the healing of skin tissues.

It is yet another object of the invention to provide collagen/glycosaminoglycan compositions that promote skin tissue healing.

It is still another object of the invention to induce improved rates of skin tissue repair by contacting wounds with an aqueous colloidal suspension of collagen and a glycosaminoglycan.

It is yet another object of the invention to induce the healing of previously intractable wounds.

Other objects and advantages of the invention will become apparent from the following detailed description and the claims appended hereto.

DETAILED DESCRIPTION OF THE INVENTION

The present invention provides an aqueous dispersion of collagen and a glycosaminoglycan (of a special class as hereinafter defined) for use on wounds to promote the healing thereof. Most usually the aqueous phase is a standard saline solution, i.e., an isotonic salt solution, however water alone may also be used.

As noted, besides the aqueous phase, there are two essential components in the compositions. The first of the essential components is collagen.

Collagen is a proteinaceous material comprising the major fibrous element of mammalian skin, bone, tendon, cartilage, blood vessels, and teeth. Its biological purpose is to hold cells together in discrete units; and secondarily it has a directive role in developing tissues. The collagen proteins are distinctive in their physical characteristics in that they form insoluble fibers possessing high tensile strength. It is the fibrous nature of the collagen that serves to hold the various body structures and components together.

While the basic molecular structure of collagen may be modified to meet the needs of particular tissues, all collagens are organized into a common structure consisting of three polypeptide chains that form a triple stranded helix. These triple stranded helical units, in turn, are formed into a quarter-staggered array of linearly aligned bundles which make up collagen fibers. The collagen fibers are stabilized by covalent cross-links.

It has been shown that purified collagen can be utilized medically in reconstructive and cosmetic surgery for the replacement of bony structures or gaps in bony structures, and for filling out tissues where wrinkles have formed. In such usage, collagen is secured from mammalian sources, e.g., calves, whereby extraneous proteinaceous material is removed by various dissolution, precipitation and filtration techniques to leave a pure collagenous product. Unfortunately this pure natural collagen may induce antigenic response in the host subject. Such response is generated by the end portions of the collagen fibrils which are not helically bound. Fortunately these end portions of collagen can be cleaved therefrom by treatment with a proteolytic enzyme, e.g. pepsin. After digestion with pepsin, the cleaved peptide ends are discarded and only the central collagen bundles (tropocollagen) remain. These central collagen bundles have greatly reduced antigenicity and they can be used for the purposes noted above without undue antigenic side effects.

The reduced antigenic, enzyme treated collagen is an article of commerce. It can be secured from the Collagen Corporation of Palo Alto, Calif. under the trademarked name "Zyderm." Such purified collagen is preferred in the present compositions.

Although reduced antigenic collagen is preferred, non-cleaved collagen that has been isolated from animal sources may also be used. It is only necessary that the collagen be prepared in a sterile condition in an aqueous suspension. Some inclusion of materials commonly associated with the collagen, e.g., polysaccharides, can be tolerated and do not interfere with the benefits of the wound healing compositions. Other forms of processed collagen are also useful in the compositions.

The second essential component in the present composition is a glycosaminoglycan. Glycosaminoglycans are polysaccharide materials that, in animals, form the principal component of proteoglycans found in connective tissues. Proteoglycans consist principally of the glycosaminoglycans with minor amounts of protein. Similar molecular structures are also found in plants.

The glycosaminoglycans, being polysaccharides, comprise repeating units of an amino disaccharide. The amino sugar may be a derivative of the aldose sugars, e.g., glucose, galactose in the case of animals, mannose in the case of plants etc. Some common glycosaminoglycans are heparin, heparan sulfate, keratan sulfate, chondroitin sulfate, hyaluronate, in the case of animals; and alginate, in the case of marine plants.

It should be understood however, that only certain members of the glycosaminoglycans are useful in the wound healing compositions. Specifically, those glycosaminoglycans that exhibit chemotaxis for fibroblasts or endothelial cells are useful in the present invention. Those glycosaminoglycans that exhibit no chemotaxis, or low chemotaxis, for fibroblasts or endothelial cells are not preferred for use in the present compositions.

Chemotaxis can be determined by several means. Tests can be run in Boyden chambers according to the techniques taught by Boyden in Journal of Experimental Medicine Vol. 115, p. 453 et. seq. (1962). The teachings in the publication are incorporated herein by reference. In the present instance, fibroblasts and/or endothelial cells are placed in the solution in one half of the Boyden e chamber, while the glycosaminoglycan of interest is dispersed at low concentrations (e.g. $10^{-10}$ gm/ml) in the solution in the second half of the chamber. The two halves of the chamber are separated by a semi-permeable membrane. Migration of the fibroblasts or endothelial cells to and through the semi-permeable membrane is subsequently noted by microscopic examination. Those glycosaminoglycans exhibiting a strong chemotactic effect are suitable for use in the present compositions.

In Table 1 below, there is presented some data obtained from a series of Boyden chamber tests on collagen as well as a number of glycosaminoglycans. In the tests the compounds of interest were tested at various concentrations for their ability to attract fibroblasts. Only the concentration at which the compound exhibited maximum chemotaxis is shown in the Table.

TABLE 1

| Compound | Concentration for optimal chemotaxis (gm/ml) | Fold increase in chemotaxis over control (1) |
|---|---|---|
| control (saline) | — | 1.0 |
| collagen | — | 1.0 |
| chondroitin sulfate | $1 \times 10^{-10}$ | 2.3 |
| Hyaluronic acid | $1 \times 10^{-8}$ | 2.0 |
| Alginate | $1 \times 10^{-9}$ | 8.6 |
| Heparin | $1 \times 10^{-10}$ | 3.5 |

Thus, in in vitro Boyden chamber tests, heparin and especially alginate exhibit strong chemotaxis for fibroblasts and/or endothelial cells.

In another more pertinent in vivo test technique, a piece of polyvinyl alcohol (PVA) sponge ("Ivalon") is implanted in the dermis of test animals. Test compositions, i.e. collagen and a glycosaminoglycan or control materials, e.g. collagen alone, are impregnated into various samples of the PVA sponge prior to implantation. After a period of time, e.g., seven days, the PVA sponge is retrieved from the animal, histologically sectioned and microscopically examined for invasion of cells and the deposition of extracellular matrix in the sponge mass. The extent of fibroblasts and endothetial cell infiltration is a measure of the ability of the composition to promote healing by attraction (chemotaxis) of repair cells into the area.

In one group of experiments using the in vivo test technique outlined above: PVA sponge alone; PVA sponges impregnated with collagen (8.75 mg/ml) alone in saline; or collagen (8.75 mg/ml) in combination with various glycosaminoglycans (280 µg/ml) in saline were implanted into test animals. After 7 days, the implants were removed and examined microscopically to determine the percent of sponge volume that had been invaded by new capillaries. Table 2 below sets forth the results:

TABLE 2

| Volume % vascularization at 7 days after implant. | |
| --- | --- |
| PVA sponge alone | 0.67% |
| Sponge + collagen alone | 1.20% |
| Sponge + collagen + hyaluronic acid | 1.67% |
| Sponge + collagen + chondroitin sulfate | 2.64% |
| Sponge + collagen + alginate | 5.20% |
| Sponge + collagen + heparin | 6.66% |

From the above it will be noted that compositions including heparin and alginate exhibited a marked ability to promote vascularization. Chondroitin sulfate was significantly weaker than either heparin or alginate; while collagen alone, and collagen with hyaluronic acid appeared to be only weakly active when compared to heparin or alginate.

Thus the useful compositions of the invention comprise collagen and a glycosaminoglycan that exhibits chemotaxis for fibroblasts and/or endothelial cells. It will be understood that the glycosaminoglycans can be present in combination in the compositions. For instance, heparin which exhibits a very strong ability to promote vascularization may be used in admixture with alginate, which exhibits a very strong chemotaxis for fibroblasts. Combinations of the various glycosaminoglycans may be selected to emphasize the particular chemotactic properties of the various glycosaminoglycans. Heparin, heparan sulfate, and alginate are the preferred glycosaminoglycans for use in the present compositions. Hyaluronate and chondroitin sulfate are less useful in the present compositions.

Heparin and heparan sulfate are staple pharmaceutic products, and are commercially obtainable from any number of pharmaceutical sources. Alginates are produced from sea-weeds and are also readily available from pharmaceutical sources. They are most commonly available as the salt form, e.g. sodium alginate. As used herein "alginate" refers to such salt compositions. Although the heparins and alginates are the preferred glycosaminoglycans for use in the healing compositions, it will be understood that other glycosaminoglycans are also useful, so long as they exhibit a good chemotactic effect vis-a-vis fibroblasts and/or endothelial cells.

The concentrations of collagen, and especially the glycosaminoglycan, in the aqueous dispersion must be controlled in order to achieve the maximum healing effect. In addition, the relative concentrations of the collagen and glycosaminoglycan components must be maintained within fairly well defined limits. If the collagen concentration is too high, there is an inhibition of the migration of fibroblast cells into the wound area. The presence of fibroblasts is vital to the ultimate repair of the damaged tissues. Similarly, if the glycosaminoglycan concentration is too high, undesirable local hemorrhaging or inflammation may occur. But if the glycosaminoglycan concentration is too low, fibroblast and endothelial cell migration into the wound is markedly reduced from the migration rates noted at optimum glycosaminoglycan levels.

Thus it has been determined that collagen should be present in the aqueous dispersion at an optimal concentration of about 7–10 mg/ml.; while the glycosaminoglycan(s) should be present at an optimal concentration of about 250–350 µg/ml. Considerable variation above or below the noted concentrations is permissible. Collagen concentrations can be in the range of several milligrams/milliliters up to perhaps 15–20 milligrams/milliliter. The glycosaminoglycan(s) can be in the range of perhaps 100 micrograms/milliliter up to perhaps 1000 micrograms/milliliter, so long as undue inflammation does not occur.

It is desirable to hold the concentrations close to the stated amounts to produce optimum results, and to avoid inhibitory effects or inflammatory reactions. The preferred concentration for collagen is 8.75 mg/ml, and 280 µg/ml for the glycosaminoglycan(s). It should be understood, however, that the concentrations may be varied by perhaps one-half to twice the optimal concentrations without critically impairing the usefulness of the wound healing compositions. However, at concentrations much further below or above the optimal levels, reduced effectiveness and undesireable side-effects can come into play.

The ratio of collagen to glycosaminoglycan is also important to the optimal effectiveness of the compositions. Compositions showing optimal benefit have a collagen concentration some 25–35 times greater than the glycosaminoglycan concentration. Stated in another way, the glycosaminoglycan concentration should be in the vicinity of about 3 to 4% of the collagen concentration for optimal effectiveness. If the collagen concentration in the aqueous phase is increased, then the glycosaminoglycan concentration should also be increased to maintain the desired concentration ratio. While the noted ratios are important to maintain the optimum healing effect, ratios diverging from those stated may be used, but the healing effect is diminished.

The compositions of the invention are prepared from commercially available dispersions of the individual components. Collagen is normally available as a saline suspension at a concentration of 35 mg/ml. The commercial product is diluted with sterile normal saline to the concentration levels noted above, e.g., 8.75 mg/ml. Commercial glycosaminoglycan solution is added with good mixing to the diluted collagen suspension to achieve the desired level, e.g, 280 µl/ml. The resultant colloidal suspension has a milky white appearance and has a viscosity somewhat like that of fresh egg albumen. For some purposes it may be desirable to thicken the compositions into a more viscous or semi-solid gelled state. If such is desired, standard medically acceptable gelling materials, e.g. cellulose, may be included in the compositions.

The prepared compositions should be maintained under refrigeration; but should not be frozen or maintained at room temperature. Freezing will interfere with suspension properties. Ambient temperatures may permit the growth of any minute amount of contaminants. When kept under refrigeration, the suspensions will maintain their effectiveness for extended periods, i.e. months.

Although the compositions may be used as the aqueous colloidal suspension of collagen and glycosaminoglycan, per se, it is also possible to add small amounts of an antibiotic, e.g. neomycin sulfate, normally used for topical applications. Such addition of a topical antibiotic is not necessary to promote wound healing by the present compositions. Such addition is solely as a matter of convenience in the general management of wounds.

In any event the wound healing compositions are used as follows:

The wound is first thoroughly cleansed and decontaminated as per standard medical practice and any necrotic tissue is debrided to leave as clean and sterile a wound surface as possible. A quantity of the saline-collagen-glycosaminoglycan suspension is applied liberally to all surfaces of the wound and a gauze dressing, thoroughly moistered with the wound healing composition, is placed over the wound. From time to time, e.g., once or twice a day, the dressing is removed and the wound surfaces are cleaned as in standard medical practice. The wound healing composition is then reapplied to the wound surfaces, and the wound is covered with new moist gauze dressings as noted above. This procedure is followed until new epithelial tissue completely closes the wound surface, at which time, application of the wound healing composition is discontinued.

Observation of Wound Healing Effects

As noted previously, wound healing is a complex and involved process with features including gross anatomy, microscopic processes, chemical changes, cell migration etc. The most direct and reliable method of gauging the wound repair process is histological examination. Such examination is, however, only semiquantitive. Nonetheless, histology does give a summation of all the complex processes that take place during wound healing. Therefore it can be used to best assess the benefits derived from any procedures used to improve or hasten healing.

Compositions of collodial suspensions in saline of collagen alone, and collagen with various glycosaminoglycans were applied to wounds. After seven days, a histologic assessment of the wound was made. All compositions had 8.75 mg/ml of collagen. The glycosaminoglycans were present at concentrations of about 280 μg/ml.

The following are descriptive composites of the histological assessments:
1 Collagen alone in saline: few fibroblasts; very poor neovascularization; fair degree of inflammation.
2. Collagen and heparin: virtual absence of inflammation; intense fibroplasia; extremely rich network of new capillaries and venules; the wounds at seven days gave a histologic appearance equivalent to unassisted wound repair at 3–4 weeks; extremely vascularized granulation tissue.
3. Collagen and alginate: closely similar histologically to collagen-heparin however somewhat less vascularization then collagen-heparin.
4. Collagen and chondroitin sulfate: much less vascularization then collagen-heparin and collagen-alginate; appreciable inflammation.
5. Collagen and hyaluronate: marked reduction in inflammation and fibroplasia; poor vascularization.

Both collagen-heparin and collagen-alginate preparations aggressively promoted wound healing. Collagen-chondroitin sulfate and collagen-hyaluronate preparations had a significantly reduced wound healing activity. Collagen alone had no significant activity.

In view of the excellent results obtained in animal studies, some clinical tests were undertaken with the collagen-heparin preparations. The following accounts relate the results of some of these trials:
1. A 42 year old female suffering from scleroderma had chronic, recurring foot ulcers. Prior therapy had consisted of prolonged (up to six months) bed rest and closure of the ulcer with skin grafts. In the case of a new ulcer a collagen (8.75 mg/ml) and heparin (280 μl/ml) colloidal suspension was applied daily to the ulcerated area. Well vascularized granulation tissue began to form promptly and the ulcer healed completely within 4 weeks without the need for bedrest.
2. An 85 year old male with peripheral vascular insufficiency developed a large and deep ulcer over the Achilles tendon area. Conventional therapy failed to halt the progression of the ulcer and the patient was considered to be a candidate for amputation. Treatment with the collagen-heparin composition was commenced. After 4 months of daily application of the collagen-heparin suspension, the ulcerated area was completely filled with well vascularized granulation tissue and epithelialization had taken place.
3. A 34 year old female with sickle cell disease suffered from recurring ulcers on her lower extremities. These ulcers had required bedrest and skin grafting. Upon recurrance of an ulcer, treatment with the collagen-heparin suspension was undertaken. The ulcer healed within six weeks.

What is claimed is:

1. A method for promoting the healing of a surface wound, which method comprises:
    applying to the wound surface, a liquid aqueous suspension of collagen fibrils in admixture with a minor amount of a glycosaminoglycan wherein said glycosaminoglycan is chemotactic for fibroblasts or endothelial cells and the collagen is not covalently crosslinked to the glycosaminoglycan, wherein said liquid aqueous suspension is applied repeatedly to the wound surface during the healing to effectively promote the healing process.

2. The method of claim 1 wherein two or more glycosaminoglycans are combined in the suspension.

3. The method of claim 2 wherein the combined glycosaminoglycans are heparin and alginate.

4. The method of claim 1 wherein the glycosaminoglycan is heparin.

5. The method of claim 1 wherein the glycosaminoglycan is heparan sulfate.

6. The method of claim 1 wherein the glycosaminoglycan is an alginate.

7. The method of claim 1 wherein the suspension is a saline suspension.

8. The method of claim 1 wherein the suspension is gelled.

9. The method of claim 1 wherein the collagen is present in the suspension in concentrations in the order of about 7 to 10 milligrams per milliliter.

10. The method of claim 1 wherein the glycosaminoglycan is present in chemotactically effective amounts.

11. The method of claim 10 wherein the glycosaminoglycan is present in the suspension in concentrations in the order of about 100 to 1000 micrograms per milliliter.

12. The method of claim 1 wherein the glycosaminoglycan is present in the suspension in a concentration of about 250–350 micrograms per milliliter.

13. The method of claim 1 wherein the ratio of concentration of collagen to glycosaminoglycan is about 25–35 to 1.

14. A method for promoting the healing of a surface wound, which method comprises, applying to the wound surface a suspension of fibrils, itself comprised of an admixture of:
(1) collagen; and glycan, wherein the glycosaminoglycan
(2) a minor amount of a glycosaminoglycan, is chemotactic for fibroblasts or endothelial cells and the collagen is not covalently crosslinked to the glycosaminoglycan, wherein the suspension of the fibrils is applied repeatedly to the wound surface during the healing to effectively promote the healing process.

15. The method of claim 14 wherein the suspension of fibrils is a liquid suspension of fibrils.

16. The method of claim 15 wherein the liquid suspension of fibrils is an aqueous suspension.

17. A method for promoting the healing of a surface wound, which method comprises, applying to the wound surface a suspension of fibrils, itself consisting essentially of an admixture of:
(1) collagen; and
(2) a minor amount of a glycosaminoglyclan, wherein the glycosaminoglycan is chemotactic for fibroblasts or endothelial cells and the collagen is not covalently crosslinked to the glycosaminoglycan, wherein additional suspension of particles is applied a number of times to the wound surface during the healing to effectively control the healing process.

18. The method of claim 17 wherein the suspension of particles is a liquid suspension of fibrils.

19. The method of claim 18 wherein the liquid suspension of fibrils is an aqueous suspension.

20. A method for promoting the healing of a surface wound, which method comprises, applying to the wound surface a suspension of fibrils, itself comprised of an admixture of:
(1) a major amount of collagen, wherein the collagen is selected from collagen fibrils which is not covalently crosslinked or from collagen which is lightly covalently crosslinked; and
(2) a minor amount of glycosaminoglycan, wherein the glycosaminoglycan is chemotactic for fibroblasts or endothelial cells and the collagen is not covalently crosslinked to the glycosaminoglycan, wherein additional suspension of fibrils is applied repeatedly to the wound surface during the healing to effectively promote the healing process.

21. The method of claim 20 wherein the suspension of fibrils is a liquid suspension of fibrils.

22. The method of claim 21 wherein the liquid suspension of fibrils is an aqueous suspension.

23. A method for promoting the healing of a surface wound which method comprises:
applying repeatedly to the wound surface a liquid aqueous suspension of of collagen fibrils in admixture with glycosaminoglycan wherein said glycosaminoglycan is chemotactic for fibroblasts or endothelial cells and the collagen is not covalently crosslinked to the glycosaminoglycan, wherein the amounts of collagen and glycosaminoglycan in the suspension are sufficient to promote healing, wherein the amount of collagen is below that which produces an inhibition of the migration of the cells into the wound area, and the amount of glycosaminoglycan is below that which produces undesirable local inflammation or hemorrhaging.

24. A method for promoting the healing of a surface wound, which method comprises, applying repeatedly to the wound surface a suspension of fibrils, itself comprised of an admixture of:
(1) collagen fibrils; and
(2) a glycosaminoglycan, wherein the glycosaminoglycan is chemotactic for fibroblasts or endothelial cells and the collagen is not covalently crosslinked to the glycosaminoglycan, wherein the suspension of fibrils is applied repeatedly to the wound surface during the healing process, wherein the amounts of collagen and glycosaminoglycan in the suspension are sufficient to promote healing, the amount of collagen is below that which produces an inhibition of the migration of the cells into the wound area, and the amount glycosaminoglycan is below that which produces undesirable local inflammation or hemorrhaging.

25. A composition for use in promoting the healing of a surface wound, comprising a liquid aqueous suspension of a major amount of fibrils of collagen, in admixture with a minor amount of a glycosaminoglycan that exhibits a chemotactic effect on fibroblasts or endothelial cells, wherein the collagen is not covalently crosslinked to the glycosaminoglylcan.

26. The composition of claim 25 wherein two or more glycosaminoglycans are present in the suspension.

27. The composition of claim 26 wherein heparin and alginate are admixed together in the suspension.

28. The composition of claim 25 wherein normal saline solution is the suspending component.

29. The composition of claim 25 wherein the aqueous suspension is gelled.

30. A composition for use in promoting the healing of a surface wound, comprising a liquid aqueous suspension of fibrils of collagen in admixture with a glycosaminoglycan that exhibits a chemotactic effect on fibroblasts or endothelial cells, wherein the collagen is not covalently crosslinked to the glycosaminoglycan and the collagen is present in the suspension at a concentration of about 7 to 10 milligrams per milliliter.

31. A composition for use in promoting the healing of a surface wound, comprising a liquid aqueous suspension of fibrils of collagen, in admixture with a glycosaminoglycan that exhibits a chemotactic effect on fibroblasts or endothelial cells, wherein the collagen is not covalently crosslinked to the glycosaminoglycan, and the glycosaminoglycan is present in the suspension at a concentration of from about 100 to about 1000 micrograms per milliliter.

32. A composition for use in promoting the healing of a surface wound, comprising a liquid aqueous suspension of fibrils of collagen in admixture with a glycosaminoglycan that exhibits a chemotactic effect on fibroblasts or endothelial cells, wherein the collagen is not covalently crosslinked to the glycosaminoglycan, and the glycosaminoglycan is present in the suspension at a concentration of about several hundred micrograms per milliliter.

33. A composition for use in promoting the healing of a surface wound, comprising a liquid aqueous suspension of fibrils of collagen in admixture with a glycosaminoglycan that exhibits a chemotactic effect on fibroblasts or endothelial cells, wherein the collagen is not covalently crosslinked to the glycosaminoglycan, and the ratio of the concentration of collagen to the concentration of glycosaminoglycan is about 25-35 to 1 by weight.

34. The composition of claim 33 wherein the glycosaminoglycan is heparin.

35. The composition of claim 33 wherein the glycosaminoglycan is heparan sulfate.

36. The composition of claim 33 wherein the glycosaminoglycan is an alginate.

37. A composition comprising a major amount of collagen in fibril form, in admixture with a minor amount of heparin, and sufficient water or saline to suspend the collagen and the heparin, wherein the collagen is not covalently crosslinked to the heparin.

38. The composition of claim 37 wherein the composition is chemotactic for fibroblasts or endothelial cells.

39. The composition of claim 37 wherein collagen is present at about 7-10 milligrams per milliliter and heparin is present at about 250-350 micrograms per milliliter.

40. A composition comprising a major amount of collagen in fibril form in admixture with a minor amount of an alginate, and sufficient water or saline to suspend the collagen and alginate.

41. The composition of claim 40 wherein the composition is chemotactic for fibroblasts or endothelial cells.

42. The composition of claim 40 wherein collagen is present at about 7-10 milligrams per milliliter and the alginate is present at about 250-350 micrograms per milliliter.

43. A composition comprising a major amount of collagen in fibril form in admixture with a minor amount of a combination of heparin and alginate, and sufficient water or saline to crosslinked to the heparin and alginate wherein the collagen is not covalently suspend the collagen, heparin and alginate.

44. The composition of claim 43 wherein the composition is chemotactic for fibroblasts or endothelial cells.

45. The composition of claim 32 wherein collagen is present at about 7-10 milligrams per milliliter and the heparin and alginate are present in a combined total of about 250-350 micrograms per milliliter.

46. A composition comprising collagen in fibril form in admixture with glycosaminoglycan, wherein the collagen is not covalently crosslinked to the glycosaminoglyclan, wherein the amounts of collagen and glycosaminoglycan in the suspension are sufficient to promote healing, the amount of collagen is below that which produces an inhibition of the migration of the cells into the wound area, and the amount of glycosaminoglycan is below that amount which produces undesirable local inflammation or hemorrhaging.

* * * * *